United States Patent [19]

Ayer

[11] 4,332,257
[45] Jun. 1, 1982

[54] MEDICAL CLIP AND ELECTRODE CONSTRUCTIONS

[75] Inventor: George E. Ayer, Naperville, Ill.

[73] Assignee: Bunker Ramo Corporation, Oak Brook, Ill.

[21] Appl. No.: 120,422

[22] Filed: Feb. 11, 1980

[51] Int. Cl.³ ............................................. A61B 5/04
[52] U.S. Cl. .................................. 128/640; 128/641
[58] Field of Search ............................ 128/639–641, 128/643, 644, 783, 791–793, 798, 802, 803

[56] References Cited

U.S. PATENT DOCUMENTS

| | | | |
|---|---|---|---|
| 505,561 | 9/1893 | Smith | 128/783 |
| 909,481 | 1/1909 | Tregoning | 339/261 |
| 1,195,079 | 8/1916 | Peterson | 339/261 |
| 1,294,656 | 2/1919 | Hammond | 339/261 |
| 1,651,294 | 11/1927 | Rumore | 339/261 |
| 2,438,350 | 3/1948 | Reichard | 339/108 |
| 2,516,657 | 7/1950 | Spendlove | 339/108 |
| 2,529,270 | 11/1950 | Webster | 339/108 |
| 2,677,117 | 4/1954 | Swain | 339/110 |
| 2,685,881 | 10/1954 | Kelly | 128/802 |
| 2,702,892 | 2/1955 | Youger | 339/108 |
| 2,714,196 | 7/1955 | Melehan | 339/97 |
| 2,782,786 | 2/1957 | Krasno | 128/639 |
| 2,815,749 | 12/1957 | Friedman | 128/644 |
| 2,831,174 | 4/1958 | Hilmo | 128/802 X |
| 2,969,519 | 1/1961 | Thomas | 339/33 |
| 3,022,483 | 2/1962 | Youger | 339/108 |
| 3,072,877 | 1/1963 | Landwehr | 339/108 |
| 3,087,486 | 4/1963 | Kilpatrick | 128/785 |
| 3,182,257 | 5/1965 | Linkowski | 324/149 |
| 3,201,746 | 8/1965 | Askew | 339/108 |
| 3,420,223 | 1/1969 | Day et al. | 128/639 |
| 3,574,305 | 4/1971 | Muhl | 128/639 |
| 3,599,629 | 8/1971 | Gordy | 128/640 |
| 3,606,881 | 9/1971 | Woodson | 128/641 |
| 3,651,447 | 3/1972 | Branco et al. | 339/102 R |
| 3,662,322 | 5/1972 | Morrison | 339/95 B |
| 3,677,268 | 7/1972 | Reeves | 128/803 |
| 3,740,703 | 6/1973 | Sessions | 339/255 P |
| 3,750,094 | 7/1973 | Zenkich | 339/217 R |
| 3,774,143 | 11/1973 | Lopin | 339/61 R |
| 3,821,689 | 6/1974 | Graham | 339/31 T |
| 3,829,826 | 8/1974 | Brown | 339/255 R |
| 4,016,869 | 4/1977 | Reichenberger | 128/640 |
| 4,029,381 | 6/1977 | Tarrall et al. | 339/61 R |
| 4,040,697 | 8/1977 | Ramsay | 339/61 R |
| 4,051,842 | 10/1977 | Hazel et al. | 128/640 |
| 4,072,388 | 2/1978 | Dunn | 339/103 R |
| 4,082,087 | 4/1978 | Howson | 128/640 |
| 4,090,760 | 5/1978 | Furey | 128/639 X |
| 4,097,104 | 6/1978 | Furey et al. | 128/639 X |
| 4,109,648 | 8/1978 | Larke | 128/639 |
| 4,126,126 | 11/1978 | Bere et al. | 128/640 |
| 4,165,141 | 8/1979 | Williams et al. | 339/75 R |
| 4,239,046 | 12/1980 | Ong | 128/640 |

FOREIGN PATENT DOCUMENTS 1490489 8/1969 Fed. Rep. of Germany .
292340 6/1928 United Kingdom .

Primary Examiner—Lee S. Cohen
Attorney, Agent, or Firm—Nicholas A. Camasto; John R. Hoffman

[57] ABSTRACT

Terminal clip and electrode constructions are disclosed for use with lead wires of instruments such as medical monitoring instruments which employ electrodes for attaching to a patient. The terminal clip includes a conductive member having a hook portion for engaging a terminal portion of the electrode. The electrode includes a terminal portion for grasping by the conductive hook portion of the terminal clip, and a loop for embracing the terminal clip housing to hold the terminal clip in position and prevent relative movement between the conductive hook of the clip and the terminal portion of the electrode. The terminal portion and the loop of the electrode are fabricated of a collapsible-memory material, such as heat formed Mylar or the like. The terminal portion of the electrode is coated with a conductive ink for electrical connection between a patient and the terminal clip.

25 Claims, 6 Drawing Figures

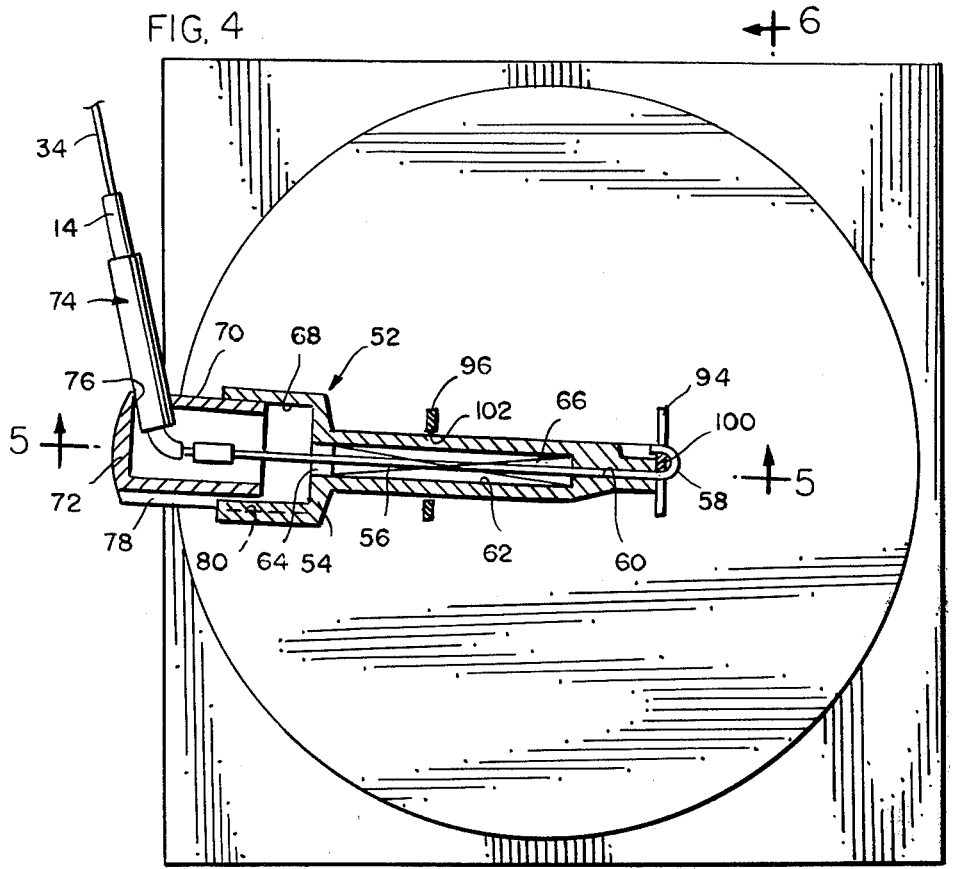
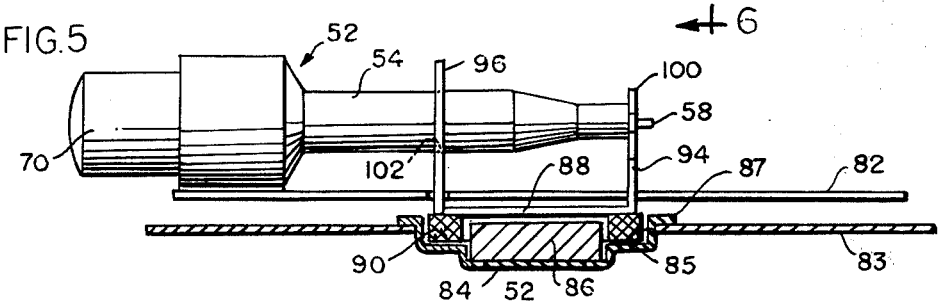
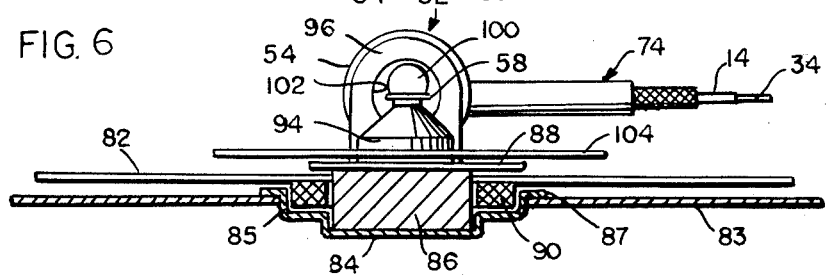

MEDICAL CLIP AND ELECTRODE CONSTRUCTIONS

BACKGROUND OF THE INVENTION

This invention relates to terminal clip and electrode constructions for mechanically and electrically connecting lead wires associated with medical equipment to electrodes adapted for attachment to an anatomical body member of a patient.

Such electrodes are well known in the medical field and typically comprise a conductive male projection having an enlarged head for association with a terminal clip. The electrode normally includes a base carried by a patch, or the like, adhesively secured to various portions of a patient's body which are to be monitored by the medical equipment, such as left arm, right arm, left leg, right leg, and particular torso areas. The electrodes are then connected, by terminal clips, to a lead wire of a medical machine or instrument, such as an electrocardiographic machine.

One of the problems with terminal clip and electrode constructions of the character described, is the tendency of the terminal clips to become disengaged with the male projections of the electrodes due to manipulation during a monitoring operation or patient movement. Many terminal clips heretofore available simply are too easily removed or dislodged from the male projecting terminal portion of the electrode because of inadequate grasping by the clip and the construction of the terminal portion of the electrode.

Another problem with terminal clip and electrode constructions of the character described, is that relative movement between the terminal portion of the clip and the terminal portion of the electrode is easily caused by patient movement, for instance, during a monitoring operation. This relative movement or "rubbing" between the terminal portions causes friction which effects electrical noise in the monitoring equipment which, in turn, interferes with the monitoring function and read out of the monitoring machine.

This invention, in part, is directed to providing new and improved terminal clip and electrode constructions which resist accidental removal or disengagement. The electrode also prevents relative movement between the terminal clip and electrode terminals and thereby eliminates the above described electrical noise in the monitoring equipment.

In addition, in carrying out the above improvements certain projecting portions of the electrode are utilized. These projecting portions are fabricated of a collapsible-memory material so that the projections collapse should a patient roll over, for instance, and yet return to their normal operative positions.

An object, therefor, of the present invention is to provide a new and improved electrode construction for securing to various portions of a patient's body, and including novel means cooperating with a terminal clip for holding the terminal clip in engagement with the electrode.

Another object of the invention is to provide a new and improved electrode construction of the character described, which prevents relative movement between the terminal portion of the clip and the terminal portion of the electrode to thereby eliminate friction therebetween which might cause electrical noise in the equipment during a monitoring operation.

SUMMARY OF THE INVENTION

More particularly, terminal clips are shown for use with lead wires of instruments such as medical monitoring instruments, or the like, which employ electrodes of the general type having a graspable terminal portion and means for attaching the electrode to a patient. The terminal clip includes a support member, and a conductive member adapted for grasping the terminal portion of an electrode. The conductive member includes a conductive hook portion at the distal end thereof.

An electrode constructed in accordance with the invention includes a terminal portion which has a projecting closed loop graspable by the hook portion on the distal end of the terminal clip conductive member. The electrode also includes means for holding the terminal clip in position with the conductive member thereof securely in engagement with the terminal loop of the electrode. With this construction, the terminal clip is held in engagement with the electrode, and the conductive member of the clip and the terminal portion of the electrode are held against relative movement which might cause electrical noise in the monitoring equipment.

Furthermore, the terminal portion of the electrode and the means for holding the terminal clip on the electrode are fabricated of Mylar material which is heat formed to have a collapsible memory. The terminal portion is coated with a conductive ink for electrical connection between a patient and the terminal clip.

Other objects, features and advantages of the invention will be apparent from the following detailed description taken in connection with the accompanying drawings.

DESCRIPTION OF THE DRAWINGS

FIG. 4 is a longitudinal central sectional view through a terminal clip in engagement with an alternate form of electrode in accordance with the present invention;

FIG. 5 is a vertical sectional view taken generally along the line 5—5 of FIG. 4, with the terminal clip thereof shown in elevation; and FIG. 6 is a vertical sectional view taken generally along the line 6—6 of FIG. 4, with the terminal clip thereof shown in elevation.

DETAILED DESCRIPTION OF THE INVENTION

Figure 1:
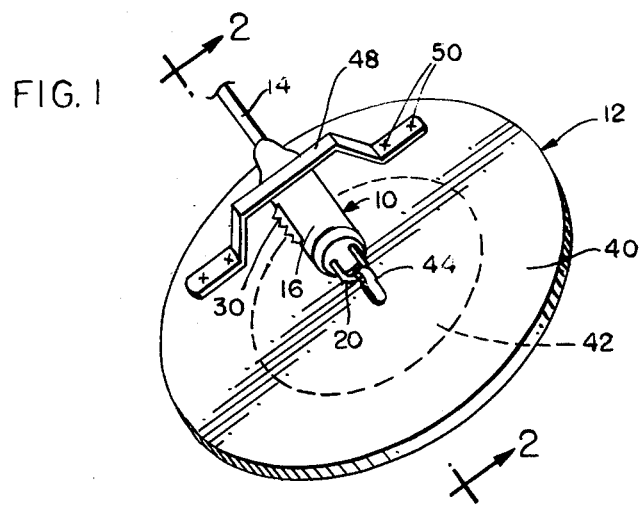
FIG. 1 is a perspective view of a terminal clip in engagement with an electrode in accordance with the present invention.

Referring to the drawings in greater detail, and first to FIG. 1, a terminal clip, generally designated 10, and an electrode, generally designated 12, are shown for use with instruments such as medical monitoring instruments or the like.

Terminal clip 10 is connected to a lead wire 14 from a medical monitoring instrument (not shown) and for electrical termination with electrode 12 as well as with electrodes of the general type having a graspable terminal portion and means for attaching the electrode to a patient. More particularly, the terminal clip includes a support member or housing 16. A conductive member 18 (FIG. 3) is slidably mounted in housing 16 and has an integral conductive hook portion 20 at the distal end thereof. The conductive member is slidably received in an aperture 22 (FIG. 3) at the front of housing 16.

Figure 3:
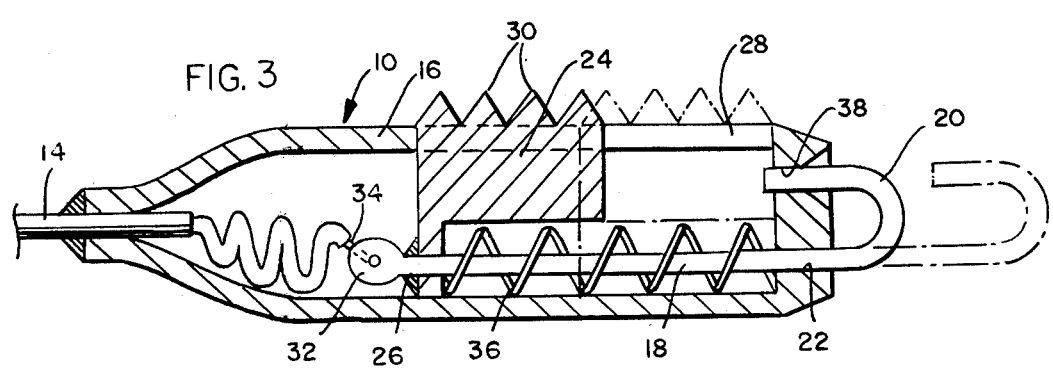
FIG. 3 is an enlarged central sectional view of the terminal clip of FIGS. 1 and 2, showing the extended position of the conductive element thereof in phantom.

Referring particularly to FIG. 3, a slide member 24 is secured to conductive member 18, as at 26, for moving the conductive member relative to support member 16. The slide member protrudes through an elongated slot 28 in support member 16 with a portion exteriorly exposed for manual manipulation by an operator's thumb. The exposed portion of the slide member is serrated, as at 30, to facilitate manual manipulation thereof.

Conductive member 18 has an enlarged portion 32 at the rear end thereof electrically connected to a core 34 of lead wire 14.

A coil spring 36 is disposed within support member 16 and bears at one end thereof against the inner front end of the support member, and at the other end thereof against slide member 24 which is securely fixed to conductive member 18.

Figure 2:
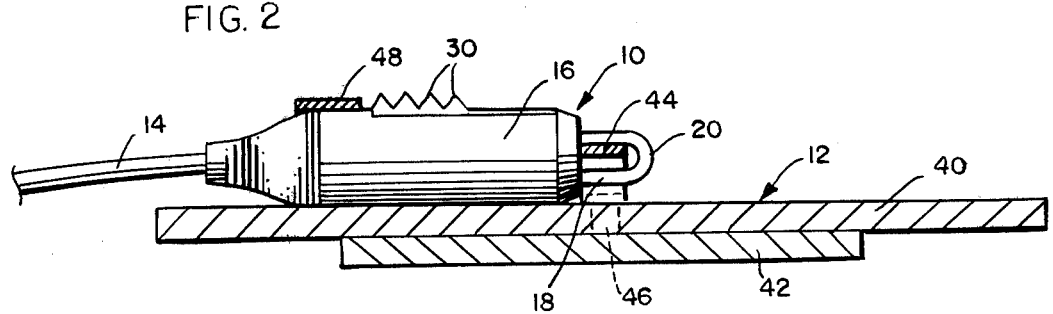
FIG. 2 is a vertical sectional view through the electrode of FIG. 1, with the terminal clip not in section.

With the above described construction of terminal clip 10 shown in FIGS. 1–3, it can be seen that conductive member 18 is movable by slide member 24 from a retracted position shown by the full lines in FIG. 3, to an extended position shown in phantom. In the extended position, the hook portion at the distal end of conductive member 18 can easily grasp a terminal portion of an electrode. In its retracted position, the hook portion can securely hold the terminal portion of an electrode. Spring 36 will effectively bias the conductive member toward its retracted position to facilitate securely holding the terminal portion of a wide variety of electrode constructions. Support member 16 also has a through aperture 38 at the forward end thereof so as to receive the turned-back end of hook portion 20 and is capable of forming a closed loop for completely surrounding an electrode terminal portion.

Referring to FIGS. 1 and 2, electrode 12 includes an adhesive pad 40 for attachment to an anatomical body member of a patient. As is known, the pad may comprise a "peel strip" for protecting the adhesive on the pad prior to attachment to a patient. A conductive disc 42 is secured to a portion of the underside of the adhesive pad for engaging the patient. A terminal portion 44 defines a relatively small loop member disposed on the top of the adhesive pad for grasping by conductive hook portion 20 of terminal clip 10. The terminal portion is electrically coupled to conductive disc 42 by appropriate conductive means 46 extending through adhesive pad 40.

Means in the form of a generally elastic strap 48 is secured to the top of adhesive pad 40 by appropriate means, such as stitching 50. Strap 48 is provided for embracing support member 16 of terminal clip 10 to hold the terminal clip against the top of electrode 12, with the terminal clip in engagement with the terminal portion of the electrode. This is particularly important in order to prevent relative movement between the clip and the electrode which might cause electrical noise in the monitoring equipment, as will be discussed in greater detail hereinafter.

Referring to FIGS. 4 and 5, another form of terminal clip and electrode combination is shown. More particularly, a terminal clip, generally designated 52, includes a support member 54 which slidably receives a conductive member 56 having a conductive hook portion 58 at the outer distal end thereof. The support member has a bore 60 at the front end thereof slidably receiving the conductive member, and an enlarged bore 62, behind bore 60, within which a plug member 64 is slidably received. The plug member is securely fixed to conductive member 56 for movement therewith and for positioning the rear end of the conductive member within support member 54. Spring means 66 is disposed within bore 62 and bears at its rear end against plug 64 to bias the conductive member toward its retracted position shown in FIGS. 5 and 6.

Support member 54 is open at its rear end and defines a cylinder 68 within which is mounted a piston-like slide member 70 for moving conductive member 56 from its retracted position to its extended position. Slide member 70 has a closed rear end 72 defining a push-button against which an operator's thumb may be engaged for moving the conductive member. A quick-disconnect coupling means, generally designated 74, is fixedly secured within an aperture 76 to slide member 70 and is electrically coupled to the rear end of conductive member 56. The quick-disconnect means is adapted for electrical connection to lead wire 14 from the medical monitoring instrument. Slide member 70 has a keying rib 78 extending radially outwardly into a keying slot 80 of support member 54 for preventing relative rotation of the slide member.

The electrode shown in FIGS. 4 and 5 includes an adhesive pad 82, similar to pad 40 in FIGS. 1 and 2, for attachment to an anatomical body member of a patient. A peel strip 83 is secured to the underside of the adhesive pad for protecting the adhesive on the pad prior to attachment to a patient. A Mylar cap 84 protrudes through an aperture 85 in the peel strip and has an outwardly protruding peripheral flange 87 which bears against the top of the adhesive pad. The cap is removable with the peel strip. At this point, it should be noted that the components of the electrode are shown in FIG. 6 in a somewhat exploded view to facilitate the illustration. Cap 84 surrounds a conductive gel pad 86 which is directly engageable with a patient, after the peel strip and cap are removed, and picks up pulses from the patient, and transmits the pulses to a base portion 88 of a generally U-shaped terminal member of the electrode. A dielectric closed-cell plastic foam ring 90 is disposed within cap 84 about conductive pad 86 to center the pad within the cap. The ring adheres to the sides of the conductive gel pad.

The U-shaped terminal member of the electrode shown in FIGS. 4 and 5 includes a first, protruding terminal portion 94 and a second, protruding support member engaging loop portion 96, both of which are integral with base portion 88. Terminal portion 94 is similar to the terminal portion 44 shown in FIGS. 1 and 2, in that it is adapted for grasping by hook portion 58 of conductive member 56 of terminal clip 52. Loop portion 96 is similar to strap 48 of the electrode shown in FIGS. 1 and 2, in that it is adapted for embracing support member 54 of terminal clip 52 and holding the terminal clip non-movably on top of the electrode with the conductive member in engagement with terminal loop portion 94 of the electrode.

The U-shaped terminal member, including portions 94 and 96 and integral base portion 88, is fabricated of Mylar material with printed conductive ink thereon to establish a conductive path from conductive gel pad 86 to the terminal portion of clip 52. This is a much less expensive construction than fabricating the entire U-shaped terminal member of solid conductive matrial, such as metal. In addition the Mylar material can be heat formed to have a spring memory and yet be collapsible. For instance, should a patient roll over onto the electrode, the protruding portions thereof will collapse and not stick the patient and yet will return to their normal positions.

Turning to FIG. 6, the U-shaped terminal member is shown in an end view as grasped by terminal clip 52. More particularly, terminal portion 94 has an enlarged head portion 100 and is grasped therebeneath by hook portion 58 of terminal clip 52. The support member engaging loop portion 96 of the U-shaped terminal member has a hole 102 through which the front of housing 54 of terminal clip 52 protrudes. Thus, the terminal clip is embraced and held against the top of the electrode with hook portion 58 of the terminal clip in engagement with terminal portion 94 of the electrode to prevent relative movement therebetween which might cause electrical noise in the monitoring equipment.

The electrode shown in FIG. 6 is different from that shown in FIGS. 4 and 5 in that it includes a second adhesive disc 104 which engages the top of base portion 88 of the U-shaped terminal member to securely hold the same in assembled position on top of the electrode in engagement with conductive gel pad 86. As with the electrode structure of FIGS. 4 and 5, peel strip 83 and cap 84 are removable so that conductive gel pad 86 is directly engageable with a patient.

From the above, it is readily apparent that new and improved electrode constructions for use in combination with terminal clips are provided. The use of means such as strap 48 in the electrode structure of FIGS. 1-3, and loop 96 in the electrode structure of FIGS. 4-6, are effective to engage and hold the connector clips against the top of the electrodes to prevent relative movement therebetween. In this manner, relative movement between the terminal portions of the terminal clips and the terminal portions of the electrodes is substantially eliminated. Consequently, rubbing or friction between the terminal portions during a monitoring operation is eliminated, along with any resulting electrical noise in the monitoring instrument which could otherwise occur from friction created by the rubbing action.

Furthermore, the Mylar printed circuit electrode terminal construction of FIGS. 4-6 provides an inexpensive conductive path from the patient to the terminal clip. This construction can collapse under the weight of a patient and yet return to normal condition for engagement and termination with a terminal clip.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. A terminal clip and electrode set for use with instruments such as medical monitoring instruments or the like, comprising:
    a terminal clip including a support member, and a conductive member mounted on the support member and adapted for engaging terminal means of an electrode; and
    an electrode adapted for attachment to an anatomical body member of a patient, said electrode including terminal means for engaging said conductive member of said terminal clip, and means remote from said terminal means for engaging said support member of said terminal clip to hold said terminal clip in position with said conductive member in engagement with said terminal means of the electrode and to prevent relative movement therebetween.

2. The set of claim 1, wherein said support member engaging means on said electrode comprises a loop member which is of a size such that at least a portion of said support member is insertable therethrough.

3. The set of claim 2, wherein said loop member is formed by a generally flexible strap.

4. The set of claim 2, wherein said terminal means of said electrode is formed in part by a projecting second loop member graspable by said conductive member of said terminal clip.

5. The set of claim 4, wherein said conductive member of said terminal clip includes a hook portion at the distal end thereof for grasping said second loop member of said electrode.

6. The set of claim 5, wherein said conductive member of said terminal clip is mounted on said support member for movement relative thereto between an extended position for easily grasping said electrode terminal means and a retracted position for securely holding said terminal means, and including means for moving said conductive member between said positions.

7. The set of claim 1, wherein said means for engaging said support member of said terminal clip and said terminal means project outwardly of said electrode and are fabricated of a collapsible-memory material to permit collapsing thereof under pressure and return thereof to normal operative conditions.

8. The set of claim 7, wherein said engaging means is fabricated of material such as heat formed Mylar.

9. The set of claim 8, wherein said terminal means of said electrode is coated with conductive material to establish electrical connection between a patient and the terminal clip.

10. The set of claim 1, wherein said terminal means of said electrode is fabricated of dielectric material which is coated with a conductive material to establish electrical connection between a patient and the terminal clip.

11. A terminal clip and electrode set for use with instruments such as medical monitoring instruments or the like, comprising:
    a terminal clip including a support member, and a conductive member mounted on the support member and adapted for engaging terminal means of an electrode; and
    an electrode adapted for attachment to an anatomical body member of a patient, said electrode including a generally U-shaped member having two leg portions and an integral bight portion, one leg portion comprising terminal means for engaging said conductive member of said terminal clip, and the other leg portion comprising means for engaging said support member of said terminal clip to hold said terminal clip with said conductive member in engagement with said terminal means of the electrode.

12. The set of claim 11, wherein said U-shaped member is fabricated of a collapsible-memory material to permit said leg portions to collapse under pressure and return to normal operative conditions.

13. The set of claim 12, wherein said U-shaped member is fabricated of material such as heat formed Mylar.

14. The set of claim 13, wherein said one leg portion which defines said terminal means is coated with conductive material.

15. An electrode for use with a terminal clip which is coupled to a lead wire of an instrument such as a medical monitoring instrument or the like, said terminal clip including a support member and a conductive member mounted on the support member, said electrode comprising:

means for attaching the electrode to an anatomical body member of a patient;

a terminal portion connected to said attaching means for engaging said conductive member of said terminal clip, said terminal portion allowing electrical connection with the patient; and means remote from said terminal portion for engaging said terminal clip to hold the clip in position with the conductive member thereof in engagement with said terminal portion of the electrode and to prevent relative movement therebetween.

16. The electrode of claim 15, wherein said terminal clip engaging means on said electrode comprises a loop member through which at least a portion of said terminal clip is insertable.

17. The electrode of claim 16, wherein said loop member is formed by a generally flexible strap.

18. The electrode of claim 16, wherein said terminal portion of said electrode is formed in part by a projecting second loop member graspable by said conductive member of said terminal clip.

19. The electrode of claim 15, wherein said means for engaging said terminal clip project outwardly of said electrode and are fabricated of a collapsible-memory material to permit collapsing thereof under pressure and return thereof to normal operative conditions.

20. The electrode of claim 15 wherein said terminal portion of said electrode is coated with conductive material.

21. An electrode for use with a terminal clip which is coupled to a lead wire of an instrument such as a medical monitoring instrument, or the like, said terminal clip including a support member and a conductive member mounted on the support member, said electrode comprising:

means for attaching the electrode to an anatomical body member of a patient; and a generally U-shaped member connected to said attaching means and allowing electrical connection with the patient, said U-shaped member having two leg portions and an integral bight portion, one leg portion comprising a terminal portion for engaging said conductive member of said terminal clip, and the other leg portion comprising means for engaging said support member to hold the clip with the conductive member thereof in engagement with said terminal portion of the electrode.

22. The electrode of claim 21, wherein said U-shaped member is fabricated of a collapsible-memory material to permit said leg portions to collapse under pressure and return to normal conditions.

23. The electrode of claim 22, wherein said U-shaped member is fabricated of material such as heat formed Mylar.

24. The electrode of claim 23, wherein said one leg portion which defines said terminal portion is coated with conductive material.

25. The electrode of claim 24, wherein said one leg portion and said bight portion of said U-shaped member are coated with conductive material to establish electrical connection between a patient and the terminal clip.

* * * * *